United States Patent [19]

Gruber et al.

[11] Patent Number: 5,503,974
[45] Date of Patent: Apr. 2, 1996

[54] RETROVIRUS DETECTION

[75] Inventors: Harry E. Gruber, San Diego; Douglas J. Jolly, San Diego, both of Calif.; Hwei-Sing Kwang, Hastings, Nebr.

[73] Assignee: University of California, Alameda, Calif.

[21] Appl. No.: 106,145

[22] Filed: Aug. 13, 1993

Related U.S. Application Data

[63] Continuation of Ser. No. 16,664, Feb. 10, 1993, abandoned, which is a continuation of Ser. No. 373,458, Jun. 30, 1989, abandoned.

[51] Int. Cl.$^6$ .......................... C12Q 1/70; G01N 33/567; G01N 33/53; G01N 33/555
[52] U.S. Cl. ...................... 435/5; 435/7.21; 435/7.24
[58] Field of Search .................. 435/5, 7.24, 7.21

[56] References Cited

FOREIGN PATENT DOCUMENTS

| | | | |
|---|---|---|---|
| 8600922 | 2/1986 | WIPO | C12N 1/00 |
| PCT8600922 | 2/1986 | WIPO | C12N 1/00 |
| 8911285 | 11/1989 | WIPO | |
| 9002797 | 3/1990 | WIPO | |

OTHER PUBLICATIONS

Gruber, et al, 1985, "Retroviral Vector–Mediated Gene Transfer . . . " Science 230: 1057–1061.
Stierle, et al, 1987, "Parvovirus Associated Antigen in the . . . " Annals Rheum. Disease 46:219–223.
Miller, et al, 1986, "Redesign of Retrovirus Packaging . . . " Mol. & Cell. Biol. 6(8): 2895–2902.
Milewski, *Recombinant DNA Technical Bulletin*, 9(2):88 (1986).
Ledley, F., *The Journal of Pediatrics*, 110(1):1 (1987).
Callahan et al., *Science*, 228:1208 (1985).
*Annals of the Rheumatic Diseases*, 46:219–223 (1987).
Bardwick et al., *Arthritis Rheum.*, 23:626 (1980).
Brassfield et al., *Arthritis Rheum.*, 25:930 (1982).
Weiss, R., *RNA Tumor Viruses*, vol. I, pp. 209–260 (Cold Spring Harbor Laboratory, New York).
Eckner and Ketrick, J. of Virology, 24:383–390 (1979).
Norval et al., Ann. Rheum. Dis. 38:507 (1979).
Hart et al., Ann. Rheum. Dis., 38:514 (1979).
Broder et al., Ann. Rev. Immunol., 3:321 (1985).
Gruber et al., Science 230:1057–1061 (1985).
Miller et al., *Proc. Natl. Acad. Sci.USA*, 80:4709–4713 (1983).
Yee, J. K., *Gene* 53:97–104 (1987).
Mann et al. *Cell* 33:153–159 (1983).
Watanabe et al., *Molecular and Cellular Biology* 3(12):2241–2249 (1983).
Watanabe et al., *Proc. Natl. Acad. Sci. USA* 79:5986–5990 (1982).
Watanabwe et al., *Eukaryotic Viral Vectors*, pp. 115–121, edited by Y. Gluzman, cold Spring Harbor Laboratory, NY, USA (1982).
Linial, *J. of Virology* 38(1);380–382 (1981).
Miller and Buttimore, *Molec. Cell Biol.* 6:2895–2902 (1986).
Willis et al., *J. Biol. Chem.* 259:7842–7849 (1984).
Miller et al., *Molec. Cell Biol.* 5:431–437 (1985).
Price, J., et al. *Proc. Natl. Acad. Aci. USA* , 84:156–160 (1987).
Kunkel, T., *Proc. Natl. Acad Sci. USA* 82:448 (1985).
Journal of General Virology, vol. 67, part 7, issued Jul. 1986, W. Ostertag et al., "The Myeloproliferative Sarcoma Virus Retains Transforming Functions after Introduction of a Dominant Selectable Marker Gene", pp. 1361–1371 . See Abstract p. 1361.

*Primary Examiner*—Christine M. Nucker
*Assistant Examiner*—Lynette F. Smith
*Attorney, Agent, or Firm*—Knobbe, Martens, Olson & Bear

[57] ABSTRACT

A method, and groups of cells and retroviruses useful in the performance of the method, of testing for the presence or amount of a first retrovirus in a specimen. A replication defective retroviral construct having a marker sequence is exposed to the specimen and the presence or amount of a recombinant retrovirus carrying the marker sequence is tested for. The replication defective vector may be disposed in cells, with the specimen being tested for the presence or amount of a retrovirus, or it may be disposed in a retrovirus, with the specimen being a group of cells which are tested for the presence or amount of said first retrovirus. In either case, where a first retrovirus complements the defective vector, a recombinant retrovirus carrying the marker sequence will be produced. The first retrovirus to be tested for may be of a previously known, or unknown type, and may be any of a group of retroviruses.

21 Claims, 1 Drawing Sheet

DELETION MUTANTS IN THE MLV GENOME
FOR THE MINIMAL COMPLEMENTATION ASSAY

EXPRESSION VECTOR FOR THE
AMPHOTROPIC ENVELOPE GENE

RETROVIRUS DETECTION

This application is a continuation of application Ser. No. 08/016,664, filed on Feb. 10, 1993, now abandoned which was a file wrapper continuation application of Ser. No. 07/373,458, filed on Jun. 30, 1989 now abandoned.

FIELD OF THE INVENTION

This invention relates to retroviruses. It further relates to a method of testing for the presence of a retrovirus in a specimen, typically a previously unknown retrovirus, and to techniques of testing for rheumatoid arthritis based upon the presence of a retrovirus.

BACKGROUND

Retroviruses are single-stranded RNA viruses. Upon infection of a cell by a retrovirus the retroviral RNA genome is transcribed into its corresponding double-stranded DNA by a reverse transcriptase enzyme which is coded for by the viral genome. This DNA then enters the nucleus and integrates into the host DNA using an integrase enzyme which is also coded for by the viral genome. The integrated viral DNA ("proviral" DNA) becomes a component of the host genome, replicating with it and being passed on to daughter cells in a stable manner. The proviral DNA is also in general transcribed to give viral RNA molecules which code for the major viral proteins, namely the gag, pol and env proteins (the "packaging proteins"). The full length RNA transcript can be packaged by the viral proteins into a viral particle which then buds off in a piece of cell membrane, in which are embedded env-derived peptides. This membrane-coated viral particle is a fully competent viral particle and can go on to infect other cells.

The genome of a retrovirus (in either the RNA or DNA form) can be divided conceptually into two parts. The first, or "trans-acting," category consists of the regions coding for viral proteins. These include the group specific antigen ("gag") gene for synthesis of the core coat proteins, the "pol" gene for the synthesis of various enzymes (such as reverse transcriptase), and the envelope ("env") gene for the synthesis of envelope glycoproteins. Other proteins may also be produced in different retroviruses from messages produced by various internal splicing reactions. These viral functions determine a considerable part of the host specificity of a virus. In the murine leukemia virus ("MLV") family, for example, the env gene products interact with cell surface receptors and determine whether the virus is ecotropic (infects only mice and rats), xenotropic (infects non-mouse species only), or amphotropic (infects mouse and other species, including human), and it has been suggested that the host range of a virus can be altered by replacing its env protein (see Milewski, *Recombinant DNA Technical Bulletin*, Volume 9, Number 2, page 88 (1986)). The gag gene products define specificity in mice with respect to two main types: N (NIH derived mice) or B (Balb/C derived mice).

In general, the second part of the retroviral genome is referred to as the "cis-acting" portion and consists of the regions which must be on the genome to allow its packaging and replication. This includes the packaging signal on an RNA molecule, such as the viral RNA, which identifies that RNA molecule to viral proteins as one to be encapsidated, Long Terminal Repeats ("LTRs") with promoters and polyadenylation sites, and two start sites for DNA replication. The promoters, enhancers, and other regions of the LTRs are also capable of conferring tissue specificity such that the virus will only be "expressed" (i.e., transcribed and translated) in specific cell types even though it may infect others.

It has been recognized that the cis-acting elements are grouped at either end of the viral genome, in or near the LTRs. Thus, the internal or "trans-acting" part of a cloned provirus might be replaced by a gene of choice to create a "vector construct" (see for example, F. Ledley, *The Journal of Pediatrics*, Vol. 110, No. 1, p. 1 (January, 1987)). When the vector construct is placed in a cell where necessary viral proteins are present, transcribed RNA should be packaged as viral particles which, in turn, will bud off from the cell. These particles will be indistinguishable in appearance from native virus particles, although they carry only the RNA of the vector construct into a cell and integrate it within that cell's genome. It is believed that the gene will then be functional in the new cell but, without the trans-acting part of the viral genome, will be incapable of expressing those proteins required for further virus production. Hence, the vector construct and the virus carrying it are "replication defective" normally being unable to produce new viral particles in the cell. The vector construct can, however, be transcribed and express its gene product.

Retroviruses are known to be widely spread in non-human species and the cause of various pathogenic conditions. However, only a very small number of retroviruses have been identified in humans, and these only recently. In addition, new retroviral sequences have been detected in cells of human origin (see Callahan et al., Science, Vol. 228, p. 1208; 1985), although their significance remains unknown.

The cause of many human pathogenic conditions remains unknown. One such pathogenic condition is human rheumatoid arthritis ("RA"). In various studies, viruses have been found to be present in body fluids from some human subjects suffering from RA, who were studied as part of a larger group of RA subjects. However, the results in such studies have been inconclusive in that, typically, a majority of the subjects did not exhibit the presence of the virus identified in the minority. For example, parvovirus has been demonstrated in RA synovial fluid in a minority of RA suffering patients. *Annals of The Rheumatic Diseases*, 46:219–223 (1987). Epstein-Barr ("EB") virus infection also appears to be present in a majority of patients with RA, but in no higher percentage than in the normal population, although RA patients are apparently less able to regulate such infections than normal control subjects (Bardwick et al., *Arthritis .Rheum.*, Vol. 23, p. 626, 1980). A retrovirus has been identified by Brassfield et al., *Arthritis Rheum*, Vol. 25, p. 930 (1982), as the apparent cause of caprine arthritis, a goat arthritis clinically similar to human rheumatoid arthritis.

Previously, the standard techniques used in an effort to determine the presence of an unknown retrovirus (e.g. one whose presence may be suspected but which has not previously been isolated or characterized) have been a reverse transcriptase assay, electron microscopy, and various immunologic and nucleic acid hybridization assays. For example, such techniques have been described by Weiss, R. (1982) in *RNA Tumor Viruses* Vol. I, pages 209–260 (Cold Spring Harbor Laboratory, N.Y.).

Complementation assays have been used to titer retroviruses that have already been isolated and characterized. In other words, complementation assays are used to determine the ability of a known retrovirus to have a specific biologic effect. For example, in the S+ L− assay a murine leukemia virus rescues a MSV replication-deficient virus, infects an untransformed cell line and thereby induces a transformation event, Eckner and Kettrick, *J. of Virology*, Vol. 24, p. 383–90 (1979). Such assays are time consuming, are highly dependent on the ability of the viruses to complement and the ability of the recipient cell to be transformed, and are subjective in view of the necessity to assess cell morphology associated with the transformed state. In addition, these assays deal with known, characterized retroviruses and are used simply to titer those viruses.

As pointed out by Norval et al., *Ann. Rheum. Dis.*, Vol. 38, p.507 (1979) and Hart et al., *Ann. Rheum. Dis.*, Vol. 38, p. 514 (1979), the presence of a retrovirus in a majority of patients with RA has not been demonstrated, despite extensive efforts to determine the cause of RA. The failure to detect a retrovirus which is clearly associated with RA, or retroviruses associated with other human pathogenic conditions of unknown etiology, could be the result of relative insensitivity of both the reverse transcriptase assay and electron microscopy, and the limitation of immunologic and nucleic acid hybridization assays which only search for virus proteins or nucleic acid sequences very closely related to those known to exist. Further, many retroviruses can only grow in a few specific cell types, further exacerbating the difficulty in detecting previously unknown retroviruses. For example, it is known that human T-cell lymphotrophic viruses types I and II (HTLV I and HTLV II) can only be effectively grown in certain cells such as in T-cell growth factor-driven lymphocytes, or cell lines derived therefrom, as described by Broder et al., *Ann, Rev. Imunol.*, Vol. 3, p. 321 (1985).

Retroviral constructs (i.e. retroviruses carrying vector constructs) such as those described by Gruber et al., *Science*, Vol. 230, p. 1057–1061 (1985), including pLPLM, have been developed as vehicles for gene replacement therapy. The plasmid pLPLM, a murine leukemia virus-derived construct, has retroviral promoters (LTRs) and packaging signals, but the pol, gag and env genes have been deleted and replaced by cDNA for human hypoxanthine phosphoribosyltransferase ("HPRT"). A. D. Miller et al., *Proc. Natl. Acad. Sci. USA*, ("PNAS") Vol. 80, p. 4709–4713 (1983); J. K. Yee, *Gene*, Vol. 53, p. 97–104. It is known that when viral constructs having the LTRs, packaging signal, and a gene of interest, are placed in a cell having a genome coding for a retrovirus with the packaging signal deleted (known as a "helper cell"), such retrovirus will pseudotype the RNA transcribed from the vector construct, which carries a packaging signal, into a recombinant retrovirus (a retrovirus carrying a replication defective retroviral vector, is sometimes referred to herein as a retroviral particle). See, e.g., PCT application No. WO 86/00922, published Feb. 13, 1986; *Molecular Biology of Tumor Viruses, Second Edition*, "RNA Tumor Viruses" Robert Weiss (Ed) Cold Spring Harbor Laboratory, Cold Spring Harbor, N.Y., USA (1984); Mann et al., *Cell*, Vol. 33, p. 153–159 (May 1983); Watanabe et al., *Molecular and Cellular Biology*, Vol. 3, No. 12, p. 2241–2249 (Dec., 1983); Watanabe et al., *Proc. Natl. Acad. Sci., USA*, Vol. 79, p. 5986–5990 (October, 1982); and Watanabe et al., *Eukaryotic Viral Vectors*, p. 115–121, editor Y. Gluzman, Cold Spring Harbor Laboratory, Cold Spring Harbor, N.Y., USA (1982). In addition, replication defective retroviral genes have been rescued from cells by infecting the cells with a suitable retrovirus known to be present. Even if the defective vector sequences are not appropriate to the rescuing viral proteins, such rescue happens at an appreciable frequency compared to the frequency of a fully compatible defective vector (0.01%–1%). For example, see Linial, *Journal of Virology*, Vol. 38, No. 1, p. 380–382 (April, 1981). Since a fully compatible defective vector will give signals of about $10^6$ units/ml, frequencies described above should be easily detectable.

SUMMARY OF THE INVENTION

The present invention provides a method of testing either laboratory or clinical specimens for the presence or amount of a retrovirus (sometimes referred to herein as a "first" retrovirus). The specimen, or a portion thereof, is brought into contact with a retroviral vector which carries a marker and which does not have the ability to replicate. The vector is carried by either a retrovirus or a cell (i.e., the proviral form of the vector). The first retrovirus may be either a known or previously unknown retrovirus (an "unknown retrovirus" being one which has not previously been isolated and characterized). That is, in the case where the specimen is a sample to be tested for the presence of a retrovirus, the sample is not otherwise known to carry a retrovirus. In the case where the specimen is a group of cells, the cells are not otherwise known to be carrying the retrovirus. In the method described and claimed herein a first retrovirus, if present, complements the test reagent replication defective retroviral vector so that a recombinant retrovirus may be produced which carries the marker (the marker being selected so that its presence can be conveniently determined). The replication defective retroviral vector used will be one with an encapsidation (i.e., packaging) signal, a marker sequence, and other required sequences (generally the 3' and 5' LTRs) so that when carried to a cell, and in the presence of the requisite enzymes, the defective vector can be integrated into the cell's genome and express the marker. The defective vector may optionally additionally code for other proteins, including any of the gag, pol, or env proteins, required to produce a complete retrovirus carrying the retroviral vector with the marker gene. However, it will be understood that the defective vector is "defective" in the sense that it is unable, in primary cells which may be used to receive both the first and defective viral vectors, to produce complete viruses which can go on to infect secondary cells. Thus, the defective vector will not code for all proteins necessary to produce further retroviruses therefrom.

In the practice of the invention, a test medium which contains primary cells or a retrovirus carrying the defective vector construct is contacted with a specimen which is to be tested for a first retrovirus such that the first retrovirus (if present in the specimen), may complement the replication defective retroviral vector and produce a recombinant retrovirus carrying the marker sequence. The production of a recombinant retrovirus carrying the marker is then tested for. It will be understood that in the case where a specimen is to be tested for a previously unknown type of retrovirus, it will not be known for certain whether in fact that retrovirus will complement the replication defective vector at a detectable frequency. However, in the case where a specimen is being tested for a particular type of known retrovirus, then the replication defective vector can be selected so that such complementation is likely to be obtained.

In a preferred case, whether the first retrovirus is known or unknown, the defective vector can be designed to code for all packaging proteins, other than one. In this situation the chances of detecting the first retrovirus may be increased, since the first retrovirus need only provide a minimum complementation in the form of a single suitable packaging protein which will complement the missing packaging protein. In an alternative arrangement, a plurality of groups of replication defective retroviral vectors can be exposed to the specimen or a portion thereof, the retroviral vectors of each group having a marker sequence and a sequence which codes for a corresponding packaging protein different from the packaging protein coded for by the sequences of the remaining groups, all of the groups together having sequences which code for all packaging proteins required to produce a recombinant retrovirus carrying the marker sequence. Thus, portions of the specimen would be tested against respective groups so that the members of the groups cannot complement one another. A single specimen portion could be tested against several groups which together carry all but one packaging protein (so that the members of the group cannot completely complement one another). In these arrangements, the retrovirus being tested for may complement the retroviruses of some groups better than others, and thus overall the chances of detecting the first retrovirus may be increased. This would be particularly true where the first retrovirus is of an unknown type.

In one preferred embodiment of the invention, primary cells which carry the replication defective retroviral vector (in the proviral form) are cultured with the test specimen. Complementation of the defective vector may be obtained directly or indirectly from a first retrovirus which infects the primary cells. Direct complementation results from expression by the first retrovirus, following its integration into the primary cell genome, of the required protein (or proteins) for packaging and replication. Indirect complementation results from expression of the required protein (or proteins) from the primary cell genome following activation by an exogenous agent (e.g., IL-1, IL-2 or other protein) which may be associated with the first retrovirus. It will be appreciated that the specimen can be patient cells to be tested for a first retrovirus and that, in such case, for example, the defective retroviral construct can be carried as a vector into those patient cells.

Secondary cells may then be cultured with medium from the primary cells. If a first retrovirus was present in the specimen and the primary cells are susceptible to infection by it, recombinant retroviruses (i.e. retroviral particles) may be produced in the primary cells and enter the medium, which recombinant retrovirus will carry the marker sequence. If the secondary cells are susceptible to the recombinant retrovirus, they will infect those cells and incorporate the marker sequence into the secondary cells. The presence of the marker sequence in the secondary cells is tested for as an indication of the presence of a retrovirus in the specimen.

In the case where the method is used to test for the presence of a particular type of retrovirus in a specimen, primary cells can be chosen which are known to be susceptible to infection by that type of retrovirus. Likewise, secondary cells would be chosen which are known to be susceptible to infection by a recombinant retrovirus produced from the primary cells and in which the marker sequence will be expressed.

Various marker sequences can be chosen. However, the marker which will be expressed in the secondary cells is preferably a sequence encoding a protein selected from: (i) an enzyme; (ii) a protein which will enable growth of the secondary cells in a medium in which they would not otherwise grow; and (iii) an antigen and, in particular, one which will be expressed on the cell surface. The presence of an expressible marker sequence in the secondary cells is tested for by the presence or absence of the marker sequence translation product. For example, the marker sequence may code for HPRT and secondary cells will be selected which are deficient in HPRT. Following culturing with media from the primary cell culture, the secondary cells will be examined for their ability to grow in hypoxanthine-aminopterin-thymidine (HAT) selection medium. If the secondary cells grow in the HAT medium, this will be an indication that the specimen in fact contained a retrovirus. Of course, other marker sequences can be used, e.g., the gene for β-galactosidase or luciferase.

Where a specimen is to be tested for an unknown retrovirus, or tested for the presence of any of a group of known retroviruses, it can be useful to choose the primary cells from a plurality of different cell lines. As earlier described, a retrovirus can be highly specific as to which cells they will infect and express their corresponding proteins. Thus, in the case of testing a specimen for an unknown retrovirus, using a plurality of different cell lines increases the chances that a retrovirus, if present in the specimen, will productively infect the primary cells. For the same reasons, it may also be desirable to select secondary cells which are from a plurality of cell lines.

It is further preferable that the secondary cells are not from any of the same cell lines as the primary cells in order that the secondary cells will be easily distinguished from the primary cells. This arrangement insures that, where the secondary cells are to be cultured with primary cell medium, and in the event that some primary cells are transferred into the secondary cell culture, they can be identified and removed (such as by exposing the secondary cells to a medium which will selectively kill the primary cells). This prevents generation of a false positive test result if primary cells are accidentally transferred to the secondary cell culture. Otherwise, the determination of the presence of the marker sequence in the secondary cell culture would typically not distinguish between primary and secondary cells expressing the marker sequence.

In the case where the patient cells are used as primary cells, however, it is considered preferable to use as secondary cells the same cell type as the primary cells since it will then be likely that any pseudotyped retrovirus produced from the primary cells will infect the secondary cells.

Generally, another technique which will increase the chances of detecting an unknown retrovirus in the specimen is to provide different packaging signals for the marker sequence. Thus, an unknown retrovirus in the specimen which may pseudotype a retroviral construct with one packaging signal at a low efficiency, may pseudotype a retroviral construct with a different packaging signal at a higher efficiency.

In the case where primary cells are used which carry the replication defective retrovirus, a further technique to increase the chances of detecting a first retrovirus (particularly if of an unknown type), is to select primary cells with their genome coding for at least one packaging protein (i.e. gag, pol, env), preferably the genome of some of them coding for a packaging protein different from that coded for by the genome of others. For example, the genome of all of the primary cells could code for a retroviral construct with a marker sequence, while the genome of some of them also code for env protein, and still others instead also code for gag or pol protein. This arrangement will increase the chance that recombinant retroviruses can be produced from the primary cells upon exposure to a specimen with an unknown retrovirus, since the chances for complementation are increased. In a minimum complementation arrangement the genome of the primary cells has a retroviral construct which not only carries the marker sequence, but in addition carries the sequences required to produce all of the proteins, except one, necessary to form a recombinant retrovirus carrying the marker sequence. In such a minimum complementation arrangement, the first retrovirus being tested for need only supply the missing protein in the primary cells for production of recombinant retrovirus carrying the marker sequence to occur. Thus, the chances of producing the recombinant retrovirus in the presence of a first retrovirus (to be detected) may be increased.

A means of confirming the presence of a retrovirus where the retrovirus tested for is of a previously known type, is to culture additional primary cells with a portion of the specimen and an antibody to the known retrovirus and test for a reduced number of secondary cells carrying the marker sequence as a result of the presence of the antibody.

Further steps which may be used with the above methods include a wash of the primary cells to remove inactive recombinant retrovirus prior to culturing the secondary cells with the primary cell medium. Preferably the washing takes place about 1 day prior to this latter culturing step. This reduces the chance that any inactive recombinant retroviruses from the primary cells (which are potentially capable of binding with receptors on the secondary cells, but are incapable of productively infecting the secondary cells to express the marker sequence therein) do not interfere with productive infection of the secondary cells by live recombinant retrovirus and reduce the sensitivity of the assay. Further, the primary cells or secondary cells, or both, can be treated to enhance ability of those cells to be infected with any recombinant retrovirus, e.g., with a detergent.

The present invention also provides cells which are useful in the above detection methods.

Using the above detection methods, the present inventors have found an association of a positive result with samples from patients suffering from rheumatoid arthritis. This apparent retrovirus (or potentially a group of retroviruses or a member of such a group) is referred to throughout this application as "rheumatoid arthritis associated retrovirus" (RA retrovirus), or equivalent expressions. As a result of this discovery, the present invention also provides for the testing of rheumatoid arthritis in a human subject, which requires testing for the presence of rheumatoid arthritis associated retrovirus in the subject using methods of the present invention.

BRIEF DESCRIPTION OF THE DRAWINGS

Embodiments of the invention will be described with reference to the drawings, in which.

DETAILED DESCRIPTION OF EMBODIMENTS OF THE INVENTION

Figure 1:
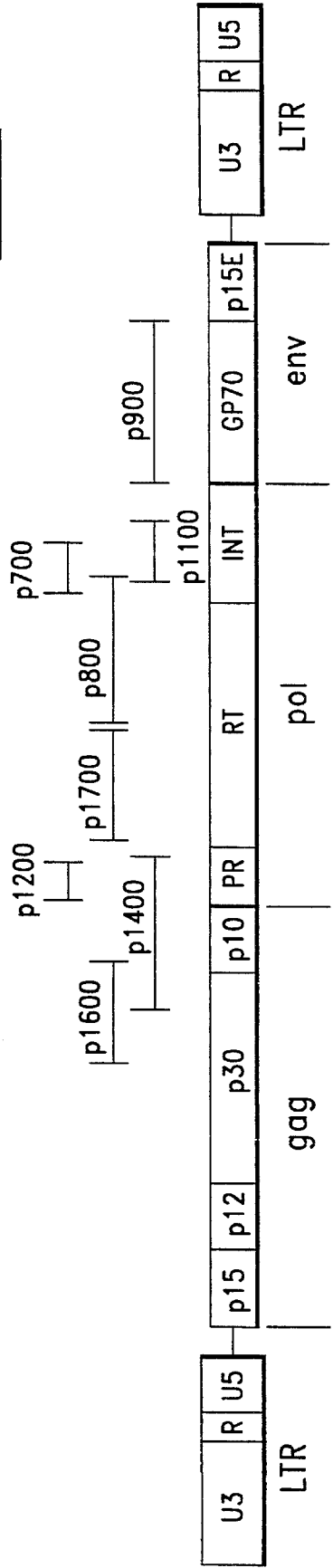
FIG. 1 illustrates a Moloney MLV genome with various deletions which can be made thereto, the resulting genomes being useful in a minimum complementation assay described below (see Example 5, below)

Fluid specimens from a number of human subjects have been evaluated for the presence of a retrovirus using the methods of the present invention. Primary cells from various cell lines were used, including an SV-40 transformed fibroblast derived from a Lesch-Nyhan child (LNSV), which was transfected with pLSΔPΔLM (the resulting recombinant cells being referred to as the LNΔP line) and selected for the HPRT-containing phenotype. pLSΔPΔLM is a plasmid carrying a murine leukemia virus-derived vector construct with LTRs and packaging signals, but without pol, gag, and env genes, which were removed and replaced by the cDNA for a mutant HPRT. pLSΔPΔLM is the same as pLPL2 (Miller & Buttimore, *Mol. Cell Biol.*, Vol. 6, p. 2895–2902 (1986)), but with the HPRT gene mutated as described by Yee et al., *Gene*, Vol. 53, p. 97–104 (1987). Another primary cell line used was an EB virus transformed lymphoblast line derived from a Lesch-Nyhan child (cell line "1547"), which cells were infected with a replication incompetent HPRT-containing retrovirus ("LPL") and selected for the HPRT-containing phenotype. The preparation of such cells is described by Willis et al., *J. Biol. Chem.*, Vol. 259, p. 7842–7849 (1984). The foregoing cell line does not spontaneously produce HPRT-containing retroviruses. A third cell line used as a primary cell source consisted of normal human cultured bone marrow, infected with a high titer preparation of a retrovirus containing the pLPLM vector construct from the producer line 7A2, as described in Gruber et al., *supra Science* (1985).

Secondary cells should be selected which are likely to be susceptible to infection by a recombinant retrovirus which may be produced from the primary cells. The secondary cell should preferably be infectable by the pseudotyping virus. In the trials below, cell lines used as secondary cells in the assays were the HPRT-deficient rat 208F or murine B77 cells (with regard to these cell lines see, respectively, Miller et al., *PNAS*, Vol. 80, p. 4709–4713 (1983) and Miller et al., *Molec. Cell. Biol.*, Vol. 5, p. 431–437, (1985)). Other cells used as secondary cells included human HPRT-deficient lymphoblasts (1547), fibroblasts (LNSV), or cultured human bone marrow cells. In the last case, the first pseudotyped retrovirus can be re-pseudotyped by superinfection of the secondary cells with murine amphotropic retrovirus (MA) (Miller et al., supra. *Mol. Cell. Biol.*, (1985)) and passage of the supernatant to 208F or B77 cell lines (which act as tertiary cells). The advantage of this procedure is that the final progeny retroviruses are known to infect the final indicator cells.

The procedure followed in testing the specimens was generally as follows. Primary cells containing the pLSΔPΔLM or vector construct were cultured with the specimen to be tested. After 3 to 5 days, supernatant from the foregoing culture was placed onto an HPRT-deficient secondary cell line and after 24 hours the cell line was grown in HAT selection medium. During storage prior to use, the secondary cell line is preselected in 6-thioguanine every four weeks to remove any HPRT-containing revertants. The primary tester line is maintained as a precautionary measure in HAT till shortly before use to ensure retention of the HPRT vector in the cell. When supernatants from LNΔP are tested on secondary cell lines such as 208F or LNSV, a further negative control (208F or LNSV alone) is always performed to check for HPRT+ revertants. The cultivation of the LNΔP cells for 3 days after adding PBLs before transferring the supernatant to secondary tester lines is a minimum time, but longer cultivation (up to 30 days) also allows detection on the secondary line of transfer of HPRT vector, sometime with a larger signal. Thus, when setting up the assay it is optimal to utilize a time course, e.g., 3, 7, 11, 14, 21, 30 days.

Control experiments were performed simultaneously with the preceding steps, wherein a medium from untreated primary cells was passaged onto the secondary cells to assure that the primary cells are not contaminating the secondary cells and that the primary cells are not spontaneously producing retroviruses carrying the marker sequence. This procedure also ensures that the secondary cell line has not developed HPRT-containing revertants. Positive controls were also run, which required exposing the primary cells to MA, followed by the passage of supernatant therefrom to the secondary cells to assure that the assay can detect retroviruses.

The secondary cell line was cultured for two weeks in HAT medium, the plates were washed, fixed in methanol, and the colonies counted. Each colony represented one HPRT-containing progeny retrovirus. The titer of retroviruses in the specimen was determined by performing limiting dilution assays with portions of the specimen.

In addition to the above procedure, further and improved sensitivity was achieved using the MA positive control as follows. Polybrene detergent was added to the 208F cell line before infection with the supernatant. The use of this detergent tended to facilitate membrane adherence and, therefore, increase the ease with which retroviruses infected the primary cells. The 208F cells were set up in microtiter wells a day before they were cultured with the specimen. The LNSV cell line, which was co-cultured with the clinical specimen, was washed the day before supernatant was transferred to the 208F secondary cells. This washing step was utilized to remove previously made, but now inactive, interfering recombinant retroviral particles. If not removed, such retroviral particles can potentially bind to, and block, receptors on the secondary cells from productive infection by live recombinant retroviruses carrying the marker sequence.

EXAMPLE 1

On day one, $2 \times 10^5$ cells from the line LNΔP were plated in DMEM plus 10% Fetal Bovine Serum on 60 mm dishes. This is the primary test line. The cells were grown in 10% $CO_2$ at 37°. On day four, polybrene was added to the media to 4 µg/ml at least 2 hours before the specimen primary blood lymphocytes (PBLs). Patient or normal blood samples with heparin as an anti-coagulant were processed rapidly (within 2 hours of being taken) and PBLs purified on histopaque. The PBLs were washed extensively (at least 3 times) to remove platelets and $10^6$ PBLs were added to each LNΔP dish in a total 4 ml DMEM+10% FBS. The positive control was 100 µl of a viral supernatant of the synthetic amphotropic murine retrovirus, MA, added to the LNΔPs; the negative control (apart from the normal individuals) was LNΔP cells with no additions. On day seven, the secondary test line (either rat 208F cells or human LNSV cells), were plated at $1-2 \times 10^5$ cells in 60 mm dish in αMEM+10% FBS+polybrene. At least 4 hours later, the supernatant was removed from the LNΔP/PBL dishes and filtered through 0.45µ filters or spun at 1500 rpm for 5 minutes in a clinical centrifuge to remove cells. 1-2 ml of clean supernatant was then added to the secondary test line, plus 2 ml of αMEM+ 10% FCS+polybrene and the cells incubated 24 hours in 5% $CO_2$ at 37°. On day eight, the medium was changed to αMEM+10% FBS plus HAT ($10^{-4}$M hypoxanthine, $2 \times 10^{-7}$M Aminopterin, $5 \times 10^{-5}$M thymidine). The medium was subsequently changed every 3 days and on day 18 the plates were washed, fixed, stained and colonies counted.

Using the above protocol, a first fifty-two clinical specimens were examined, including forty-nine synovial fluids, two synovial biopsies, and one blood sample. Most of the forty-nine fluids were from patients with RA, while the remainder included those with Reiter's Disease, osteoarthritis, gout, and a mono-articular chronic arthritis. Approximately two thirds of the RA specimens tested produced a positive result using the assay procedure described. One patient with Reiter's Disease also tested positive, but had HTLV III in his cells, as determined by nucleic acid hybridization assay. Utilization of the different cell lines described, as primary and secondary cells, did not significantly affect assay results. The titer of the retrovirus in the synovial fluid specimens was relatively constant, in the range of 1 to 30 plaques per milliliter.

Experiments also indicated that the activity in the samples from the RA patients appears to be cell-associated. In particular, plaque-forming activity was observed more consistently in the material that is sedimented by centrifugation, and not in the remaining supernatant.

Another experiment using Southern blot analysis demonstrated that the pLSΔPΔLM retroviral construct is actually transferred from the LNΔP line to the 208F cell line. In particular, the DNA was isolated from 208F cells from the above assay procedure, which are HAT resistant, and a radioactive probe made from the pLSΔPΔLM vector construct detected a corresponding four kilobase (kb) fragment on that isolated DNA, cut with the enzyme Sst I.

A further experiment used peripheral blood lymphocytes ("PBLs") isolated by FICOLL HYPAQUE gradients from a patient with RA. It was shown, that such lymphocytes can pseudotype the pLSΔPΔLM vector constructs from the LNΔP cells to the 208F cells. In a further experiment, the primary cells consisted of U937 cells carrying a retroviral vector construct termed "Bag". Cepko, *PNAS* 84:156–160 (1987). The foregoing construct contains both β-galactosidase ("Bgal") gene and the resistance gene for neomycin. A second set of U937 cells was used as the secondary cells. The primary cells were then cultured with the same PBLs from the patient of the preceding example, using the assay protocol. As shown below, the secondary cells were found to carry the beta-galactosidase gene.

EXAMPLE 2

Primary blood lymphocytes were isolated on four different occasions from one rheumatoid arthritis patient (WT), three other patients and 5 normal individuals. These were cocultivated with LNΔP cells and after three (3) days the supernatants transferred to 208F cells which were assayed for uptake of the HPRT vector by HAT selection. Column 1 of Table 1 shows the supernatants from LNΔP cultivated without patient or normal PBLs. Column 2 shows the patient or normal PBLs cultivated with LNΔP. Column 3 shows patient or normal PBL plus 1 µl (patient) or 10 µl (normals) of MA viral supernatant cultivated with LNΔP. Column 4 shows one (1) or 10 µl of MA viral supernatant cocultivated with LNΔPs. Results are expressed as the number of clones seen after 10 days of HAT selection and experiments were performed in triplicate. Unrelated 208F cells were always selected in parallel and were always completely negative (not shown).

TABLE 1

| RA Patients | 1. LNΔP Supernatant | 2. PBL on LNΔP | 3. PBL + MA on LNΔP | 4. MA LNΔP |
|---|---|---|---|---|
| WT | | | | |
| Expt. #1 | 00,00,00 | 12,07,16 | 05,07,06 | 14,09,07 |
| Expt. #2 | 00,00,00 | 06,01,02 | 04,00,06 | 03,10,07 |

TABLE 1-continued

| RA Patients | 1. LNΔP Supernatant | 2. PBL on LNΔP | 3. PBL + MA on LNΔP | 4. MA LNΔP |
|---|---|---|---|---|
| Expt. #3 | 02,00,00 | 04,07,01 | 03,09,05 | 09,15,02 |
| Expt. #4 | 00,00,00 | 05,03,06 | 06,05,10 | 10,10,05 |
| CT | 00,00,00 | 02,06,05 | 04,05,07 | 07,10,12 |
| WR | 00,00,00 | 03,04,03 | 08,12,05 | 10,12,09 |
| JC | 00,00,00 | 05,02,07 | 03,06,19 | 05,13,11 |
| Normals | | | | |
| KT | 00,00,00 | 00,00,00 | 04,--,-- | 01,--,-- |
| AG | 00,00,00 | 00,00,00 | 68,82,63 | -,100,92 |
| BS | 00,00,00 | 00,00,00 | 37,45,26 | 40,39,67 |
| JD | 00,00,00 | 00,00,00 | 17,06,-- | 108,21,38 |
| M | 00,00,00 | 00,00,00 | 42,19,31 | 26,12,35 |

EXAMPLE 3

The assay was carried out as in Example 2 except that the PBLs were cocultivated with LNΔP cells for up to 14 days and the supernatants were transferred to 208F cells at 3 and 14 days. In this case, the assays at 14 days were performed without and with pretreatment of 208F with polybrene (−polybrene, +polybrene) (TNTC=too numerous to count). The results are shown in Table 2.

TABLE 2

| | Time of cocultivation: | | |
|---|---|---|---|
| | | 14 days | |
| | 3 days | −polybrene | +polybrene |
| LNΔP (negative control) | 00,01,00 | — | — |
| MA (positive control) | TNTC | TNTC | TNTC |
| RA Patients | | | |
| 1 | 00,01,00 | 28,09,01 | 13,00,-- |
| 2 | 00,00,00 | 01,02,01 | 03,01,00 |
| 3 | 00,04,00 | 01,03,02 | 01,16,20 |
| 4 | 01,00,00 | 02,01,01 | 03,00,01 |
| 5 | 00,00,00 | 00,02,00 | 00,03,05 |

EXAMPLE 4

Primary Blood Lymphocytes from an RA patient (WT) were isolated on FICOLL HYPAQUE gradients and 5×10$^6$ cells cultivated in RPM1 1640 plus 10% FCS+PHA with 10$^4$ cfu of Bag vector (Price et al., *Proceedings of the National Academy of Sciences*, 84:156–160 (1987)), that had been shown to be helper free (<1 unit of competent virus/ml). After 3 days, 1 ml of the supernatant was transferred into U937 cells growing in the same medium and 24 hours later the cells were fixed and stained for beta galactosidase activity (Price et al., *supra*), and blue (positive) cells counted to test for transfer of the Bgal-containing vector from the PBL to the U937 cells (Experiment #1). Controls were Experiment #2: 10$^8$ units MA virus added to U937 cells, staining after 24 hours; Experiment #3: 10$^4$ units Bag vector added to U937 cells, staining after 24 hours; and Experiment #4: 10$^8$ units MA virus, 10$^4$ units Bag added to patients cells, cocultivated for 3 days, the supernatant transferred to U937 cells, stained after 24 hours. Previous experiments showed that 10$^4$ units of Bag vector incubated in medium at 37° C. for 3 days had no detectable infective activity on U937 cells. The results are shown in Table 3.

TABLE 3

| Experiment | Blue cells/10$^5$ U937 cells | |
|---|---|---|
| #1 (Bag + PBL) (onto U937) | 6 | 10 |
| #2 (U937 + Bag) | >10$^3$ | >10$^3$ |
| #3 (U937 + MA) | 0 | 0 |
| #4 (Bag + PBL + MA) (onto U937) | >100 | — |

Thus, the appearance of blue cells, even at a low level can be used to assay for the presence of a retrovirus in this quick (4 days) assay.

The complementation assay as used in the foregoing Examples relies on an unknown retrovirus providing complementing viral proteins to package a retroviral vector based on a murine leukemia virus (MLV) backbone. This vector has then to exit the primary cell and enter a second cell line where the presence of the vector is assayed. The packaging, exit and infection by the vector depend on the unknown viral proteins being capable of recognizing and packaging, albeit at low efficiency, a vector which may be at a large evolutionary distance from it. In addition, the envelope proteins of the unknown virus may allow only low efficiency entry into the secondary tester cell line. To increase the chances that the retrovirus being tested for will successfully complement the replication defective retroviral vector carrying the marker sequence, a minimum complementation assay was designed, a particular example of which is provided in Example 5 below.

EXAMPLE 5

In this particular example of a minimum complementation assay, complementing defective viral genomes were designed which express all but one Moloney MLV viral protein function. These are transfected into the primary tester cell line carrying the Moloney MLV vector. Thus the unknown retrovirus has only to supply one function (i.e., minimal complementation) in trans to allow production of marker vector plasmid, such as the HPRT vector in LNΔP. It is important in this context that LNΔP is not a mouse cell line, since such lines are capable of repairing such defective MLV genomes. The overall effect is to make the assay:

(1) more sensitive to a particular type of unknown retrovirus;

(2) capable of detecting a wider range of retroviral types.

A number of separate in frame deletions were made in the indicated domains of the cloned Moloney MLV genome pMLV-K (see Table 4 below and FIG. 1), by deletion of restriction enzyme fragments or by site directed oligonucleotide mutagenesis to produce 8 different genomes each with the indicated single deletion. The nucleotide numbers after the restriction sites correspond to the numbering for Moloney MLV in "RNA Tumor Viruses", Vol. 2, 1985, Cold Spring Harbor Laboratory. Preparation of deletion mutants in Table 4 below are prepared according to well known techniques. For example, see T. Maniatis, "Molecular Cloning—A Laboratory Manual", Cold Spring Harbor Laboratory, N.Y., U.S.A. (1982), and T. Kunkel, *PNAS*, Vol. 82, p. 488 (1985).

TABLE 4

DELETION MUTANTS OF Moloney MLV

| | Deletion Size | Deletion Domain | Exact Deletion bR | Amino Acid Deletion |
|---|---|---|---|---|
| 1) p700 | Hind III(4894)/Sph I (5137) | Integrase | 243 | 81 |
| 2) p800 | Sal I(3705)/Hind III (4894) | RT | 1185 | 395 |
| 3) p900 | Hpa I(5816)/Hpa I (7195) | Env | 1380 | 460 |
| 4) p1100 | Hind III(4894)/Sac II (4949) | Integrase | 54 | 18 |
| 5) p1200 | By mutagenesis | Protease | 201 | 67 |
| 6) p1600 | Bal I(1672)/Bal I (2053) | P30 | 381 | 127 |
| 7) p1400 | Bgl II(1906)/Bst E2 (2453) | P30,10,14 | 543 | 181 |
| 8) p1700 | Sta I(2689)/Sta I (3622) | RT | 933 | 311 |

Figure 2:
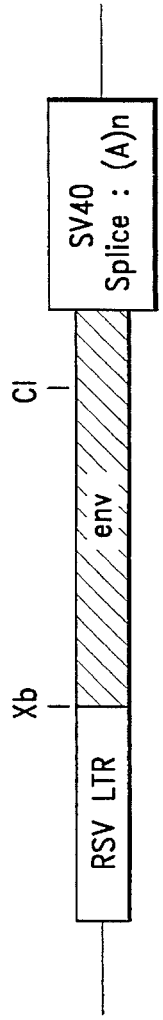
FIG. 2 illustrates an amphotrophic envelope expression vector, useful to produce an amphotrophic envelope protein for a recombinant retrovirus carrying a marker sequence (see Example 5, below).

An assay can then be performed using any of these modified LNΔP lines as before in the preceding Examples ("complementation assay"). Likewise, corresponding viral vectors could be carried in retroviruses and used in an assay to determine the presence or amount of a retrovirus in specimen cells. The complementary defective MLV and viral vector can also be provided in other suitable human or other species cell types. In addition, the secondary tester used in the preferred embodiment of the original assay is susceptible to infection with ecotropic MLV (such as pMLV-K). Moloney MLV is available from American Type Culture Collection (Rockville, Md., U.S.A.) under deposit number ATCC VR-190, the MLV-K strain can be prepared from MLV as described by Miller et al. *Molec. Cell. Biol.*, Vol. 5, p. 431–437 (1985). Thus the ecotropic envelope will "help" in this case. If other, for example, human lines are used as secondary tester lines, the primary tester line will have (in addition to the vector and complementary defective viral genome) a genome encoding an envelope capable of "helping" infection of human cells, such as the amphotropic envelope. (see FIG. 2).

Various modifications and alterations to the embodiments to the invention described above, can be envisaged by one skilled in the art. Accordingly, the present invention is not limited to the specific embodiments described above.

We claim:

1. A method of testing for the presence or amount of a retrovirus in a specimen, comprising the following steps in order:

(a) exposing a replication defective retroviral vector having a marker sequence and carried by primary cells to said specimen, in the absence of any other added virus which would allow said replication defective vector to produce a recombinant retrovirus by coinfecting said primary cells, such that a retrovirus which may be infecting said specimen can complement the replication defective retroviral vector and produce a recombinant retrovirus carrying the marker sequence;

(b) culturing said primary cells with the specimen;

(c) testing for the presence of a recombinant retrovirus; and thereby (d) determining whether said retrovirus is present in said specimen, wherein a positive result in step (c) indicates that said retrovirus is present in said specimen.

2. A method as defined in claim 1 wherein the replication defective retroviral vector is in proviral form.

3. The method of claim 1, wherein the replication defective retroviral vector carries a sequence coding for a packaging protein.

4. The method of claim 3, wherein the replication defective retroviral vector carries sequences coding for all the packaging proteins necessary for replication except for one missing packaging protein, so that the retrovirus being tested for need only produce the missing protein in order to produce the recombinant retrovirus carrying the marker sequence.

5. The method of claim 1, wherein said specimen comprises a group of cells, said method additionally comprising the step of dividing said specimen into aliquots, each of said aliquots comprising one or more cells from said group of cells, wherein each of a plurality of groups of replication defective retroviral vectors is exposed to only one of said aliquots of said specimen, the retroviral vectors of each group having a marker sequence and a sequence which codes for a packaging protein that is different from the packaging proteins coded for by the sequences of the remaining groups, and wherein the sequences which code for all the packaging proteins required to produce a recombinant retrovirus carrying said marker sequence are present in the sequences of said groups of vectors.

6. The method of claim 1, wherein the defective retroviral vector has at least one cis-acting sequence corresponding to that of a retrovirus of a type different from the retrovirus being test for.

7. The method of claim 1, wherein said specimen comprises tissue from a mammal.

8. A method as defined in claim 1 further comprising the step of washing the primary cells and further culturing the primary cells with the specimen prior to culturing the secondary cells with the primary cell medium so as to reduce the concentration of any inactive recombinant retrovirus which may otherwise be present in the primary cell medium.

9. The method of claim 1, wherein said retrovirus infecting said specimen is an unknown retrovirus.

10. A method of testing for the presence or amount of a retrovirus infecting a specimen, comprising the following steps in order:

(a) culturing said specimen with primary cells disposed in a primary cell medium which carry a replication defective retroviral vector having a marker sequence, in the absence of another added virus which would allow said replication defective vector to produce a recombinant retrovirus by coinfecting said primary cells, such that a retrovirus, if present, may complement the replication defective retroviral vector and produce a recombinant retrovirus carrying the marker sequence;

(b) culturing secondary cells with said primary cell medium so that said recombinant retrovirus carrying the marker sequence, if present, infects said secondary cells;

(c) testing for the presence or amount of the marker sequence in the secondary cells; and thereby (d) determining whether said retrovirus is present in said specimen, wherein a positive result in step (c) indicates that said retrovirus is present in said specimen.

11. A method as defined in claim 10 wherein the replication defective vector is a vector construct.

12. The method of claim 10, wherein said marker sequence is a nucleic acid sequence encoding a protein selected from the group consisting of an enzyme, a protein which will enable growth of the secondary cells in a medium in which said cells would not otherwise grow, and an antigen.

13. The method of claim 10, wherein the defective retroviral vector has a cis-acting sequence corresponding to that of a retrovirus of a type different from the retrovirus being tested for.

14. The method of claim 10, wherein the replication defective retroviral vector carries a sequence which can produce at least one packaging protein in the primary cells.

15. The method of claim 10, wherein the replication defective retroviral vector carries sequences coding for all the packaging proteins necessary for replication except one missing packaging protein, so that the retrovirus being tested for need only produce the missing protein in the primary cells to produce the recombinant retrovirus carry the marker sequence.

16. The method of claim 10, wherein the secondary cells are from different cell lines than the primary cells.

17. A method as defined in claim 10 wherein the retroviral vector constructs carried by some of the primary cells contain a different packaging signal from the retroviral vector constructs carried by others of the primary cells.

18. A method as defined in claim 10 additionally comprising treating at least one of the primary and secondary cells with a detergent to enhance the ability of the cells to be infected with a recombinant retrovirus.

19. The method of claim 10, wherein said retrovirus infecting said specimen is an unknown retrovirus.

20. The method of claims 1 or 10, wherein the primary cells used are from a plurality of different cell lines.

21. The method of claims 1 or 10, wherein the retrovirus being tested for is rheumatoid arthritis associated retrovirus.

* * * * *